United States Patent [19]

Schulz, Jr. et al.

[11] Patent Number: 4,824,980
[45] Date of Patent: Apr. 25, 1989

[54] PROCESS TO PRODUCE O-SILYL O,N-KETENE ACETALS

[75] Inventors: William J. Schulz, Jr.; John L. Speier, both of Midland, Mich.

[73] Assignee: Dow Corning Corporation, Midland, Mich.

[21] Appl. No.: 239,917

[22] Filed: Sep. 2, 1988

[51] Int. Cl.$^4$ .............................................. C07F 7/10
[52] U.S. Cl. ............................................... 556/413
[58] Field of Search ...................................... 556/413

[56] References Cited

U.S. PATENT DOCUMENTS

| | | | |
|---|---|---|---|
| 4,414,372 | 11/1983 | Farnham et al. | 526/190 |
| 4,417,034 | 11/1983 | Webster | 526/190 |
| 4,508,880 | 4/1985 | Webster | 526/190 |
| 4,692,536 | 9/1987 | Lang | 556/413 |
| 4,780,559 | 10/1988 | Quirk et al. | 556/413 UX |

OTHER PUBLICATIONS

Woodbury et al., *J. Org. Chem.*, 1978, 43, pp. 881–884.
Mahalanabis et al., *Tetrahedron Letters*, 1982, 23, pp. 3971–3974.
Green et al., *Tetrahedron Letters*, 1986, 27, pp. 535–538.
Lutsenko et al., *J. Organometal. Chem.*, 1969, 17, pp. 241–262.

*Primary Examiner*—Paul F. Shaver
*Attorney, Agent, or Firm*—Carl A. Yorimoto

[57] ABSTRACT

A process for preparing O-silyl O,N-ketene acetals having the formula,

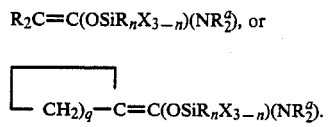

$R_2C=C(OSiR_nX_{3-n})(NR^a_2)$, or

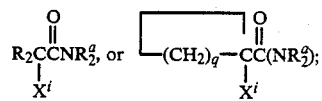

The process comprises contacting an alpha-haloamide with an alkali metal in the presence of an excess of an organohalosilane, the alpha-haloamide having the formula,

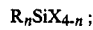

the organohalosilane having the formula, $R_nSiX_{4-n}$;

and facilitating reaction among the alpha-haloamide, the alkali metal, and the organohalosilane to form the O-silyl O,N-ketene acetal and alkali metal halides.

13 Claims, No Drawings

PROCESS TO PRODUCE O-SILYL O,N-KETENE ACETALS

BACKGROUND OF THE INVENTION

This invention relates to a process for the manufacture of O-silyl O,N-ketene acetals (SNKA), 1-organosiloxy-1-diorganoamino-2,2-diorganoethylenes. More specifically, this invention relates to a process for producing O-silyl O,N-ketene acetals from the reaction of alpha-haloamides with an alkali metal in the presence of excess organohalosilane.

For the purposes of the instant invention the term "O-silyl O,N-ketene acetal" refers to compounds of the general formula,

wherein each R and each $R^a$ is independently selected from a group consisting of alkyl, alkenyl, aryl, or aralkyl; X is a fluorine, chlorine, or bromine atom; and n is an integer from 1 to 3.

These compounds are of value becaue of their utility in the preparation of organic compunds which would be difficult to synthesize by other means. Another recent application is the use of the SNKA as acrylate polymerization initiators. This concept known as Group Transfer Polymerization (GTP) was developed by DuPont and is disclosed in three U.S. patents—U.S. Pat. No. 4,414,372, Farnham et al., issued Nov. 8, 1983; U.S. Pat. No. 4,417,034, Webster, issued Nov. 22, 1983; and U.S. Pat. No. 4,508,880, Webster, issued Apr. 2, 1985.

A primary means for preparing materials similar to SNKA cited in the art is the reaction of metalated amide enolate ions with organohalosilanes. Woodbury et al., *J. Org. Chem.*, 1978, 43, pp. 881–884, describes the reaction of lithium N,N-dialkylamide enolates with trialkylchlorosilanes. The lithium amide enolates are prepared via the reaction of the appropriate amide with tetrahydrofuran solutions of lithium diisopropylamide. The solutions are then treated with a slight excess of the trialkylchlorosilane. Mahalanabis et al., *Tetrahedron Letters*, 1982, 23, pp. 3971–3974, describes the preparation of a compound with a similar structure to an SKNA via the reaction of an N,N-dialkyl succinamide with lithium diisopropyl amide, followed by quenching with trimethylchlorosilane. Green et al., *Tetrahedron Letters*, 1986, 27, pp. 535–538, discloses the preparation of structure similar to an SNKA via the reaction of a senecioamide with lithium diisopropylamide followed by treatment with trimethylchlorosilane.

A second route to compounds with structures similar to SNKA is the interaction of ketene with silylated amines. This route is described by Lutsenko et al., *J. Organometal. Chem.*, 1969, 17, pp. 241–62.

Nowhere does the above art demonstrate or suggest the preparation of O-silyl O,N-ketene acetals from the reaction of an alpha-haloamide with an alkali metal in the presence of an excess of an organohalosilane.

SUMMARY OF THE INVENTION

The instant invention is based upon the unexpected finding that O-silyl O,N-ketene acetals having the formula,

can be prepared from the reaction of an alpha-haloamide,

with an alkali metal in the presence of excess organohalosilane,

The details of these chemical structures and the instant invention are presented, infra.

The objective of the instant invention is to provide an economical route for the preparation of SNKA that can be isolated and separated at high purity.

The instant invention has several advantages over the cited methods for preparing SNKA. Comparing the instant invention to the route in which SNKA is prepared by the reaction of an amine or amide with an appropriate metal reagent to form a metal enolate ion and subsequent reaction of the enolate ion with an organochlorosilane, the instant invention has the advantage of lower raw material costs. The art teaches the preparation of metal enolate ions via the reaction of an amine or amide with a metallic reagent such as lithium diisopropylamide or potassium hydride. Both of these metallic reagents are much more costly than the alkali metal utilized in the instant invention. The reactions can also include additional reagents such as tetrahydrofuran. The necessity for the additional reagents further adds to manufacturing cost.

DESCRIPTION OF THE INVENTION

In accordance with the instant invention there is provided a process for the preparation of O-silyl O,N-ketene acetals which are prepared under conditions described herein. What is describee, therefore, is a process for preparing O-silyl O,N-ketene acetals having the formula,

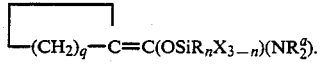

wherein each R and each $R^a$ is independently selected from a group consisting of alkyl, alkenyl, aryl, or aralkyl; X is a fluorine, chlorine, or bromine atom; and wherein n has a value of 1, 2, or 3, and q has a value of from 2 to 22, inclusive, said process comprising (A) contacting an alpha-haloamide with an alkali metal in the presence of an excess of an organohalosilane, wherein the alpha-haloamide has the formula,

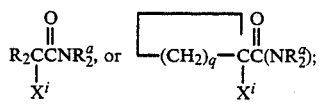

the organohalosaline has the formula,

wherein R, $R^a$, X, n and q are defined above; and wherein $X^i$ is a halogen atom; and (B) facilitating reaction among the alpha-haloamide, the alkali metal, and the organohalosilane to form the O-silyl O,N-ketene acetal and alkali metal halides, The O-silyl O,N-ketene acetal may be, for example,

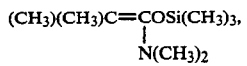

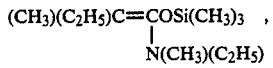

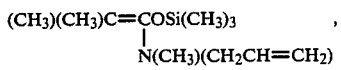

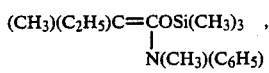

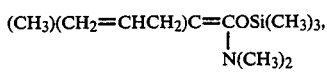

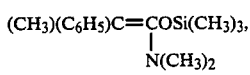

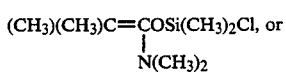

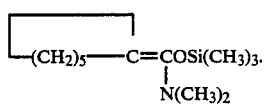

The alpha-haloamide can be, for example, N,N-dimethyl-2-bromoisobutyramide, N,N-ethylmethyl-2-chloro-2-methylbutyramide, N,N-methylallyl-2-bromoisobutyramide, N,N-methylphenyl-2-chloro-2-methylbutyramide,

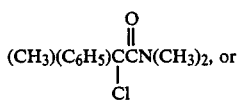

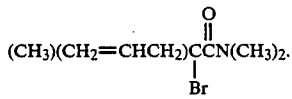

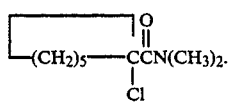

The organohalosilane may be, for example, methyltrifluorosilane, methyltrichlorosilane, dimethyldichlorosilane, trimethylchlorosilane, trimethylbromosilane, diethyldichlorosilane, triethylbromosilane, diisopropyldichlorosilane, t-butyldimethylchlorosilane, vinyltrichlorosilane, methylvinyldichlorosilane, dimethylvinylchlorosilane, phenylmethyldichlorosilane, phenyltrichlorosilane, or diphenyldichlorosilane.

The alkali metal may be, for example, lithium, sodium, potassium, or alloys thereof. The preferred alkali metal is sodium. The alkali metal may be used in the form of an alloy of two or more of the metals, such as a sodium/potassium alloy in a solid or molten form. The alkali metal may also be used in the form of a dispersion in an appropriate inert liquid, inert to the reactants or product of the instant invention, such as a paraffin. The alkali metal or an alloy of the alkali metal may also be used as a dispersion of molten particles in an inert liquid.

The reaction of an alpha-haloamide with an alkali metal (M) in the presence of an excess of an organohalosilane can be represented by the overall reaction,

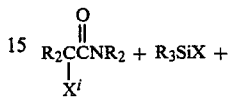

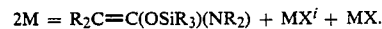

$2M = R_2C=C(OSiR_3)(NR_2) + MX^i + MX.$

The alpha-haloamide and the alkali metal are thought to form an organometallic intermediate,

This very reactive intermediate is nearly quantitatively trapped in the presence of a sufficient excess of the organohalosilane to form the desired SNKA. If the excess of the organohalosilane is not sufficient to virtually immediately trap the organometallic intermediate above, then the formation of by-products will occur instead.

The reaction among the alpha-haloamide, the alkali metal and the organohalosilane can result in the formation of a single alkali metal halide or a mixture of alkali metal halides ($MX^i$ and MX) depending upon whether or not the halide atoms on the alpha-haloamide and the organohalosilane are the same or are different. Thus, for the purposes of the instant invention, the term "alkali metal halides" refers to a single alkali metal halide or a mixture of different halides. These metal salts form a large volume of fine particles which hinder reactants from contacting the surface of the metal. Dilution with excess organohalosilane or an inert liquid and agitation aid in the contact of the reactants. The rate of reaction is greatly influenced by the exposed surface of the metal and the state of the surface of the metal. Molten alkali metal is easily dispersed in a liquid medium to present a large, highly reactive exposed area.

Contact among the reactants can occur in many modes, so long as the requirement of the presence of a sufficient excess of the organohalosilane during the reaction of the alpha-haloamide and the alkali metal is met. A first example of a mode of contact is the addition of all reactants to a batch reactor in a batchwise manner, the organohalosilane being present in a sufficient excess to maximize the production of SNKA and to serve as a diluent for the liquid/solid mixture that results. A second example of a mode of contact is the addition of a mixture of an alpha-haloamide and an organohalosilane, an essentially equimolar mixture, to an excess of the organohalosilane in an inert liquid and a molten alkali metal. A third possible mode of contact is the addition of the alpha-haloamide to a heated mixture of an excess of the organohalosilane and a molten alkali metal.

Contacting the alpha-haloamide, the organohalosilane, and the alkali metal can be carried out in a standard batch chemical reactor system. The reactor should be provided with adequate means for agitation to assure that the alkali metal is dispersed in the liquid reaction medium. For the purposes of the instant invention "facilitating reaction" means that the reactor should have provisions such as adequate agitation, heating and cooling, as necessary, adequate liquid content to assure that the slurry formed by the liquid reactants and products and solid alkali halide salts is a manageable physical mixture.

The presence of adequate liquid to assure that the mixture of reactants, product, and solid salt is a manageable physical mixture to allow sufficient contact among the reactants can be facilitated by using excess organohalosilane as a diluent. Additionally, an inert liquid, inert to the reactants and product, may be utilized as a diluent. Examples of such inert liquids are aliphatic hydrocarbons, ethers, aromatic hydrocarbons, and mineral oils.

As outlined, supra, the overall stoichiometric amount of the organohalosilane relative to the alpha-haloamide is 1.0:1. Also, as noted supra, the presence of a sufficient excess of the organohalosilane is necessary to maximize the yield of SNKA. In a batch mode in which all reactants are contacted simultaneously, the molar ratio of the organohalosilane relative to the alpha-haloamide should be greater than about 2.0:1, a stoichiometric excess of greater than about 100 percent. Preferably this stoichiometric excess should be in a range from about 100 to 400 percent. It is understood that less than a 100 percent stoichiometric excess may be utilized; however, problems such as a very heavy slurry of the liquids and solids of reaction may result causing appendant processing problems. Stoichiometric excesses of the organohalosilane greater than those disclosed above may be utilized: however, the inventors believe that no further benefit will be realized in the use of such excesses.

In the contact mode in which a mixture of an alpha-haloamide and an organohalosilane are added to a mixture of the organohalosilane and a molten alkali metal, the alpha-haloamide and the alkali metal react very rapidly and the organometallic intermediate formed reacts with the excess organohalosilane to form SNKA. The excess organohalosilane in the reactor is replenished by the organohalosilane added with the alpha-haloamide. The inventors believe that an overall excess of the organohalosilane of greater than about 10 percent on a molar basis relative to the alpha-haloamide is a sufficient excess to effect maximum conversion of the alpha-haloamide in SNKA.

As outlined, supra, the overall stoichiometric amount of the alkali metal relative to the alpha-haloamide is 2.0:1. The inventors believe that a stoichiometric excess as low as 5 percent or 2.10:1 is sufficient to essentially convert all of the alpha-haloamide to SNKA. However, the amount of alkali metal relative to the alpha-haloamide is not critical, provided that an excess of organohalosilane relative to the alpha-haloamide exists. Less than the stoichiometric amount of the alkali metal would result in unreacted alpha-haloamide, which could be separated from the desired SNKA.

When an inert liquid, in addition to the organohalosilane, is utilized, the stoichiometric excess of the organohalosilane can be reduced proportionately to a level sufficient to maximize conversion of the alpha-haloamide, as outlined supra.

The temperature of contact among the reactants affects reaction rate. However, as noted supra, the degree of conversion of the alpha-haloamide to SNKA is a function of a sufficient excess of the organohalosilane. Temperature does have an impact when it is desired to maintain the alkali metal or alkali metal alloy in a molten state. Temperature of contact can be affected by the addition of an inert liquid or the application of pressure to raise the temperature to which the liquid mixture can be heated. As an example, contact and reaction can be carried out at temperatures from ambient up to the atmospheric boiling or refluxing temperature of the organohalosilane; trimethylchlorosilane at refluxing conditions will set temperature at greater than about 58° C. A mixture of an inert liquid and an organohalosilane can be utilized to set the temperature above the melting point of the alkali metal; for example, a mixture of octane and trimethylchlorosilane can be proportioned to provide a reflux temperature greater than the melting point of sodium (97.5° C.).

The time required to complete the process is established by the temperature of the reaction mixture and the form of the alkali metal. For example, using trimethylchlorosilane as both a reactant and a solvent, temperature at reflux is about 50° to 60° C. and needed contact time to effect essentially complete reaction of the alpha-haloamide is greater than 2 hours, and often greater than about 10 hours. As a further example, a mixture of octane and trimethylchlorosilane can be made with a boiling point of about 105° C. to provide molten sodium in the reaction mixture. Under these latter conditions, time for essentially complete consumption of the alpha-haloamide could be 1 hour or less.

The process of the instant invention can further comprise isolating and separating the SNKA. Separating and isolating the SNKA can be effected by distillation of the SNKA from the liquid/solid mixture. More preferably, separating and isolating the SNKA comprises removing the alkali metal halide salts first, and then recovering the SNKA by distillation. The salts are generated at a volume of 2 moles per mole of SNKA. These salts may be removed by such known techniques as filtration of the salts from the crude reaction mixture. Any commercial filtration method such as pressure filtration can be utilized.

Recovery of the desired SNKA from the crude product mixture, before or after removal of salts, can be effected by such known techniques as distillation. It has been shown in the example, infra, that SNKA prepared by the process of the instant invention can be recovered by distillation to purities of greater than about 80 weight percent. Further, the excess organohalosilane can also be isolated and separated by distillation, facilitating possible recycle back to the pressure.

So that those skilled in the art may better understood the instant invention, the following example is presented. The example is presented as being illustrative and is not to be construed as limiting the instant invention as delineated in the claims.

EXAMPLE 1

O-silyl O,N-ketene acetal (SNKA) was prepared from the reaction of an alpha-haloamide, an alkali metal, and an organohalosilane.

Into a 50-ml flask, fitted with a mechanical agitator and a reflux condensor, was added 28.0 g (0.258 g-moles) trimethylchlorosilane, and 2.67 g (0.116 g-atom)

of sodium metal cut into pieces of about 0.2 g. The reflux condenser was fitted with an argon inlet. 10 g (0.0515 g-moles) of N,N-dimethyl-2-bromoisobutyramide was added in one portion. The N,N-dimethyl-2-bromoisobutyramide was prepared for this reaction, as described infra.

The flask was purged with argon throughout the course of the reaction. The above mixture was heated to reflux and held for 20 hours. A liquid sample was taken and analyzed by gas chromatographic techniques. A capillary gas chromatograph with a flame ionization detector was utilized to minimize product degradation during analysis. The analysis showed approximately 87.0 percent conversion of the starting alpha-bromoamide and showed that of the alpha-bromoamide consumed, 73.5 percent was converted to the SNKA, $(CH_3)_2C=[OSi(CH_3)_3][N(CH_3)_2]$.

The mixture in the flask continued to be held at reflux. A second sample was taken after a total of 40 hours at reflux. Analysis showed that 95.3 percent of the bromoamide had been consumed and showed that the SNKA yield was 80.6 percent.

The solids were removed from the reaction mixture by suction filtration. The filtrate was distilled under reduced pressure. The product have a boiling point of 65°–67° C. at 20 mm Hg. Analysis of the recovered product by gas chromatography showed that the product was greater than 80 percent SNKA.

The N,N-dimethyl-2-bromoisobutyramide was prepared from the reaction of 2-bromoisobutyryl bromide and dimethylamine. The 2-bromoisobutyryl bromide was purchased from Aldrich Chemical, Milwaukee, Wis.

Dry dimethylamine was added to hexane. 2-Bromoisobutyryl bromide was added to the amine/hexane mixture at a rate such that the mixture never exceeded 40° C. Addition of the acid bromide took about 1 hour. The entire system was held under an argon atmosphere. The reaction was allowed to mix overnight. The mixture was filtered in a laboratory suction filter. The solids were washed with additional hexane. The filtrate and wash hexane were combined, and the combined mixture was analyzed by gas chromatographic and mass spectrmetry. The desired N,N-dimethyl-2-bromoisobutyramide was identified as the major component. The hexane was removed from the mixture in a rotary evaporator. The remaining crude product was distilled under vacuum. The product had a boiling point of 59°–60° C. at 1 mm Hg. The distilled yield was 90 percent based upon the starting acid bromide.

The above results show that high yields of an O-silyl O,N-ketene acetal can be prepared from the reaction of an alpha-haloamide with an alkali metal and an excess of an organochlorosilane.

What is claimed is:

1. A process for preparing O-silyl O,N-ketene acetals having the formula, $R_2C=C(OSiR_nX_{3-n})(NR_2^a)$, or

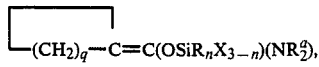

wherein each R and each $R^a$ is independently selected from a group consisting of alkyl, alkenyl, aryl, or aralkyl; X is a fluorine, chlorine, or bromine atom; and wherein n has a value of 1, 2, or 3, and q has a value of from 2 to 22, inclusive, said process comprising (A) contacting an alpha-haloamide with an alkali metal in the presence of an excess of an organohalosilane, wherein the alpha-haloamide has the formula,

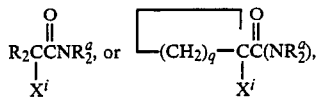

the organohalosilane has the formula, $R_nSiX_{4-n}$;

wherein R, $R^a$, X, n, and q are defined above; and wherein $X^i$ is a halogen atom; and (B) facilitating reaction among the alpha-haloamide, the alkali metal, and the organohalosilane to form the O-silyl O,N-ketene acetal and alkali metal halides.

2. A process according to claim 1, wherein the alkali metal is in a stoichiometric excess relative to the alpha-haloamide.

3. A process according to claim 1, wherein the alkali metal is selected from a group consisting of lithium, sodium, potassium, and alloys thereof.

4. A process according to claim 3, wherein the alkali metal is in a form selected from a group consisting of solid metal, solid metal in a dispersion in an inert liquid, and molten metal.

5. A process according to claim 1, further comprising isolating and separating the O-silyl O,N-ketone acetal.

6. A process according to claim 5, wherein isolating and separating the O-silyl O,N-ketene acetal comprises distillation.

7. A process according to claim 6, wherein isolating and separating the O-silyl O,N-ketene acetal further comprises removal of the alkali metal halides prior to distillation.

8. A process according to claim 1, wherein the alkali metal is a solid metal; the alkali metal is present in a stoichiometric excess of greater than about 5 percent and the organohalosilane is present at a stoichiometric excess in a range from about 100 to 400 percent, said stoichiometric excesses being relative to the alpha-haloamide; the alpha-haloamide, the alkali metal, and the organohalosilane are contacted simultaneously in a batch-wise manner; the alkali metal halides are separated from the O-silyl O,N-ketene acetal by filtration; and the O-silyl O,N-ketene acetal is separated and isolated by distillation.

9. A process according to claim 8, wherein the alpha-haloamide is N,N-dimethyl-2-bromoisobutyramide; the alkali metal is sodium; the organohalosilane is trimethylchlorosilane; and the O-silyl O,N-ketene acetal is $(CH_3)(CH_3)C=C[OSi(CH_3)_3][N(CH_3)_2]$.

10. A process according to claim 1, wherein a mixture of an alpha-haloamide and a first portion of the organohalosilane, said first portion of the organosalosilane being present in a molar proportion essentially equal to the alpha-haloamide, is added to a dispersion of a molten alkali metal in an inert liquid and a second portion of the organohalosilane; the proportions of the inert liquid and the second portion of the organohalosilane in the dispersion being controlled so that the temperature of the dispersion is above the melting point of the alkali metal.

11. A process according to claim 10, wherein the alkali metal halides are separated from the O-silyl O,N-ketene acetal by filtration; and the O-silyl O,N-ketene acetal is separated and isolation by distillation.

12. A process according to claim 1, wherein the alkali metal is molten; the alpha-haloamide is added to a mixture of the molten alkali metal and the organohalosilane; and temperature is controlled to maintain the alkali metal in a molten state.

13. A process according to claim 12, wherein the alkali metal halides are separated from the O-silyl O,N-ketone acetal by filtration; and the O-silyl O,N-ketene acetal is separated and isolated by distillation.

* * * * *